(12) United States Patent
Lindner

(10) Patent No.: US 8,470,742 B2
(45) Date of Patent: Jun. 25, 2013

(54) HOMOGENEOUS LIQUID SACCHARIDE AND OIL SYSTEMS

(75) Inventor: Gregory J Lindner, Wilmington, DE (US)

(73) Assignee: Croda Americas LLC, Wilmington, DE (US)

( * ) Notice: Subject to any disclaimer, the term of this patent is extended or adjusted under 35 U.S.C. 154(b) by 40 days.

(21) Appl. No.: 10/555,778

(22) PCT Filed: May 7, 2004

(86) PCT No.: PCT/US2004/014401
§ 371 (c)(1), (2), (4) Date: Aug. 28, 2006

(87) PCT Pub. No.: WO2004/100661
PCT Pub. Date: Nov. 25, 2004

(65) Prior Publication Data
US 2007/0129254 A1    Jun. 7, 2007

Related U.S. Application Data

(63) Continuation of application No. 10/431,616, filed on May 7, 2003.

(51) Int. Cl.
*A01N 25/04* (2006.01)

(52) U.S. Cl.
USPC .............. 504/363; 536/1.11; 536/123.13

(58) Field of Classification Search
USPC ................... 504/363; 536/1.11, 123.13
See application file for complete search history.

(56) References Cited

U.S. PATENT DOCUMENTS

| | | |
|---|---|---|
| 2,447,475 A | 8/1948 | Kaberg et al. |
| 3,455,675 A | 7/1969 | Irani |
| 3,556,762 A | 1/1971 | Hamm |
| 3,799,758 A | 3/1974 | Franz et al. |
| 3,853,530 A | 12/1974 | Franz |
| 3,868,407 A | 2/1975 | Franz et al. |
| 3,888,915 A | 6/1975 | Alt |
| 3,933,946 A | 1/1976 | Gaertner |
| 3,948,975 A | 4/1976 | Franz |
| 3,959,498 A | 5/1976 | Lyall et al. |
| 3,970,695 A | 7/1976 | Rueppel |
| 3,988,142 A | 10/1976 | Franz |
| 3,991,095 A | 11/1976 | Gaertner |
| 3,996,040 A | 12/1976 | Franz |
| 4,047,927 A | 9/1977 | Gaertner et al. |
| 4,062,699 A | 12/1977 | Armstrong |
| 4,084,954 A | 4/1978 | Rasheed et al. |
| 4,119,430 A | 10/1978 | Gaertner et al. |
| 4,120,689 A | 10/1978 | Dutra |
| 4,140,513 A | 2/1979 | Prill |
| 4,180,394 A | 12/1979 | Franz et al. |
| 4,203,756 A | 5/1980 | Gaertner |
| 4,261,727 A | 4/1981 | Dutra |
| 4,312,662 A | 1/1982 | Gaertner |
| 4,315,765 A | 2/1982 | Large |
| 4,322,239 A | 3/1982 | Dutra et al. |
| 4,341,549 A | 7/1982 | Large et al. |
| 4,397,676 A | 8/1983 | Bakel |
| 4,405,531 A | 9/1983 | Franz |
| 4,414,158 A | 11/1983 | Thummel et al. |
| 4,472,189 A | 9/1984 | Prisbylla |
| 4,481,026 A | 11/1984 | Prisbylla |
| 5,885,646 A | 3/1999 | Wong et al. |
| 5,945,377 A * | 8/1999 | Penner et al. .......... 504/362 |
| 6,451,731 B1 * | 9/2002 | Agbaje et al. .......... 504/118 |

FOREIGN PATENT DOCUMENTS

| | | |
|---|---|---|
| DE | 10064406 | 6/2002 |
| WO | 7900838 | 10/1979 |
| WO | 9503881 | 2/1995 |

OTHER PUBLICATIONS

Auda et al., Surfactant Compositions, Dec. 5, 1995, International Application Published Under the PCT, WO 95/03881 (Submitted as prior art by applicant).*

Gregory K. Dahl et al., "Adjuvant and Adjuvant Components Influence on Performance of Various Herbicides", Proc. North Cent. Weed Sci. Soc., vol. 56, 2001, p. 138, Abstract.

International Search Report for PCT/US2004/014401 dated Nov. 8, 2004.

* cited by examiner

*Primary Examiner* — Ali Soroush
(74) *Attorney, Agent, or Firm* — Jones Day

(57) ABSTRACT

Oil based emulsifiable concentrates containing a liquid saccharide including a) at least one oil component; b) at least one saccharide, particularly a liquid saccharide solution (LS); c) and at least one non-ionic surfactant. The concentrate may also contain at least one of d) at least one surfactant hydrocarbyl saccharide; or e) at least one anionic surfactant; or f) at least one additional oil soluble non-ionic surfactant. The concentrates are typically homogeneous for at least 24 hours and emulsify readily on dilution into water. The concentrates may also contain an antifoaming agent especially a polysiloxane. Upon dilution in water, the emulsions formed from the concentrates are applied to substrates in combination with agrochemically active ingredients, preferably N-phosphonomethylglycine in the form of its soluble salts, to control weeds.

20 Claims, No Drawings

HOMOGENEOUS LIQUID SACCHARIDE AND OIL SYSTEMS

CROSS REFERENCE TO RELATED APPLICATION

This application is the National Phase application of International Application No. PCT/US2004/014401, filed May 7, 2004, which designates the United States and was published in English, which is itself a continuation of U.S. Pat. No. 10/431,616, filed May 7, 2003. These applications, in their entirety, are incorporated herein by reference.

BACKGROUND OF THE INVENTION

Agrochemical compositions have been used to improve the quality and quantity of farm grown products. In this regard they can enhance biological activity and act as nutrients, growth regulators and/or pesticides, for instance as herbicides, insecticides, fungicides, or acaricides. However, since they are expensive to make and purchase, it is desirable to reduce their overall cost in use by improving their effectiveness in a unit area treated with the agrochemical.

In order to improve or enhance the effectiveness of many agrochemicals, certain materials are added to water-based agricultural spray mixtures containing the agrochemical and concurrently applied to agricultural substrates. These materials are commonly identified as agricultural spray adjuvants and exist in a wide variety of forms and compositions that are used today in commercial agriculture. These adjuvant products are used to provide a broad array of effects in typical use including, but not limited to, foam control, enhancement of the effectiveness of a specific agrochemical, and/or modification of the agricultural spray mixture for either improved stability or modulation of spray droplet diameter.

In the United States, most economically advantageous adjuvant products used to improve or enhance the efficacy of an agrochemical, primarily a pesticide, are supplied as liquids. The preferred liquid adjuvant products (for both convenience and economy) manufactured and sold in the US are supplied as concentrated liquids and fall into two primary categories. These catogories are: (1) self-emulsifying oil and surfactant compositions more commonly identified as Crop Oil Concentrates (COC), and (2) readily water soluble or dispersible surfactant formulations known as concentrated liquid Non-Ionic Surfactants (NIS). Commercial distribution channels in the US efficiently transport large volumes of such products, primarily in bulk form, making COC and NIS type products very economical for their intended use. By improving the efficacy of the more costly pesticide through its combination in spray mixtures with an economically advantageous, primarily low cost, adjuvant product, the overall economics of commercial agriculture can be improved. Use of effective adjuvant products in this manner decreases the seasonal cost to produce agricultural commodities and may also improve commodity yields, offering economic benefits to those who use them.

One of the largest single groups of such effective liquid adjuvant products sold in the United States (by volume) is a COC composition containing between 60 and 90% of a suitable agricultural grade of mineral oil; an alternate form of this adjuvant type contains a vegetable oil or methylated seed oil. All commercially significant forms of this adjuvant type commonly contain an oil soluble emulsifier composition composed of a blend of anionic and/or non-ionic surfactants that provides self-emulsification of the oil component upon dilution in a water-based agricultural spray mixture; the total surfactant concentration in a typical COC product can range from 1 to 40%, most typically between 10 and 17%.

While the oil and surfactant composition in a COC adjuvant product could also be offered as a pre-emulsified system in water (an oil-in-water emulsion), the added cost of production for an emulsified adjuvant product tends to make it less economically advantageous than the equivalent volume of oil adjuvant offered as a COC. Water based systems also have the undesirable characteristics of being generally more complicated to develop and manufacture and of requiring the use of discrete thickening, preserving, and anti-freeze systems due to the tendency of water based emulsions to support microbial growth, cream or settle/sediment, and deteriorate over time or during the freeze-thaw cycle. The effect of including water as the dispersing medium also dilutes the active components (oil and surfactant composition) making the system more expensive to deliver in the field on a pound of "active" adjuvant basis. Logistics costs also increase on this basis as more water is shipped than may otherwise be present in a comparable COC type system.

In recent times, there have been specific improvements upon the cost-effectivenss of the described economically advantageous crop oil concentrates. Most of these improvements have focused on two aspects of the composition. The first aspect is increasing the total concentration of oil soluble surfactant emulsifier which has resulted in a change in preferred surfactant concentration from 12-17% ten years ago to approximately 40% at the current time; this change was associated with a reduction in the amount of COC adjuvant product applied per unit area and resulted in improved cost-in-use attributes for the adjuvant. The second aspect is the selection of specific surfactant types based on both field data and scientific judgement; this change was associated with improved performance of the adjuvant product with specific pesticide products. PCT Publication WO 95 03881 by Auda et al describes an agrochemical crop oil concentrate containing an oil or oils, hydrocarbyl saccharide surfactant, and additional non-ionic surfactant that emulsfies readily upon dilution in water. This COC adjuvant composition was associated with enhancement or improvement of weed control performance in conjunction with soluble salts of N-phosphonomethylglycine.

More recently, U.S. Pat. No. 5,945,377 to Penner describes compositions incorporating a postemergence herbicide and a monosaccharide, particularly fructose, as a potentiator of the herbicide against weeds without decreasing tolerance of a crop plant to the herbicide. The compositions are used as a spray in water in a method for killing weeds. Although not considered an NIS adjuvant, corn syrup was evaluated as an adjuvant with several postemergence herbicides in the greenhouse and field studies. The greatest enhancement of herbicide activity was observed with high fructose corn syrup applied in combination with an ammonium sulfate and an effective non-ionic adjuvant with anionic herbicides such as glyphosate and glufosinate for control of grass species such as giant foxtail. The efficacy of the corn syrup as an adjuvant was both weed and herbicide specific.

The previously mentioned publication (WO 95 03881) describes self-dispersing alkylpolysaccharide surfactants in crop oil concentrates (COC's). These compositions did not include additional aqueous liquid non-surfactant polysaccharide components which have been found recently to promote the herbicidal activity of glyphosate. It was concluded that a robust, single phase composition containing: (1) an oil adjuvant, (2) a saccharide adjuvant, and (3) an optimal amount of surfactant with a corresponding minimum of additional water could allow the delivery of a highly concentrated liquid agricultural adjuvant product with a total surfactant concentration similar to those in use today (ca. 10-40% w/w). The successful incorporation of the inexpensive and efficacious saccharide adjuvant would improve the cost-effectiveness of the finished adjuvant product. The resulting product is commercially advantageous for the manufacturer and economically beneficial to the purchaser/user. An additional advantage for combining the saccharide and surfactant adjuvant composition with the traditional COC adjuvant composition would be the significant commercial advantage obtained by being able to provide one very broadly effective adjuvant composition having the preferred characteristics of the COC, NIS, and newer saccharide adjuvant types.

The compositions described are intended as commercial alternatives to traditional 17 and 40% surfactant in oil based COC adjuvants used in the agricultural market. These COC adjuvant types, although cost-effective for use with most water-dipsersible agrochemicals, are not the most effective type of adjuvant for the soluble salts of N-phosphonomethylglycine, most commonly called glyphosate, which represents the largest commercial pesticide sold in the US and as a result presents the largest single adjuvant sales opportunity. The most efficacious NIS adjuvants for use with glyphosate, identified as ethoxylated tallow alkylamines, are for the current time typically combined into concentrated glyphosate solution products and are therefore not readily accessible to adjuvant products intended for combination into agricultural spray mixtures. With the expiration of patents on concentrated glyphosate salt solution products, other forms of the pesticide, including products which intentionally do not include the preferred NIS adjuvant as a means to reduce the cost of formulated glyphosate and increase its concentration in solution products may also become available. It would be advantageous to alter the traditional COC product or the COC product described in WO 95 03881 to demonstrate improved efficacy enhancement with glyphosate products; this would be highly desireable as a means of expanding the market for the highly cost-effective COC adjuvant product.

Ideally it is desireable to achieve a surfactant composition that serves as both the combined COC adjuvant self-emulsifier and compatibilizer/stabilizer for the saccharide component and which also has the ability to stabilize and self-emulsify the oil alone (without the saccharide component) as well as having special advantages in that it offers improved economies in the purchase of a single surfactant composition and in enabling the flexible manufacturing of COC adjuvants in the same surfactant composition both with and without added liquid saccharide components. Since the corn syrup adjuvant also requires concurrent application of a nonionic surfactant adjuvant for optimum performance, the direct combination of the oil and corn syrup with a single surfactant system that would both "activate" the saccharide and concurrently emulsify the oil component would have the greatest economic and competitive advantage. Essentially, by using the combined COC and saccharide NIS product concept, the composition would be 100% active with a minimum total concentration of the surfactant composition required for optimum performance. Since the surfactant constitutes the most costly input for manufacturing on a component purchased price (per pound) basis, reducing surfactant to the minimum required for optimal activity is highly desireable.

The greatest difficulty in developing the combined saccharide COC adjuvant product is the identification of suitable surfactant systems which would enable the formulation of homogeneous compositions that would function both as robust stabilizers for a highly concentrated liquid saccharide solution in an oil adjuvant and which would provide the self-emulsification upon dilution that is required. These two opposing effects must be delivered in one adjuvant product with a minimum of total surfactant. Preferably a foam control agent would also be included in the composition.

In U.S. Pat. No. 5,885,646 to Wong, there is described a process for preparing nut spreads having a sugar level of from about 15 to about 50% and especially flavored nut spreads having such relatively high levels of sugar. A substantially homogeneous blend is prepared from a fluid suspension consisting essentially of an intimate mixture of sugar, liquid oil and lecithin as a surfactant to improve the fluidity of the suspension, a nut solids-containing mixture and a flavorant that is preferably added to the fluid suspension. The resulting flavored nut spreads are more fluid and softer than products made without using the fluid suspension. This invention does not provide for the characteristics of either liquid product homogeneity or self-emulsification and demonstrates a relatively high viscosity, which makes it irrelevant to this invention.

In U.S. Pat. No. 3,959,498 to Lyall there is described a one step process for applying sugar and an edible fat or oil to cereal bases. No separate step of spraying the oil into the cereal substrate is necessary. The invention also provides an emulsion cereal coating for achieving the above purpose, and a method of preparing said coating. A quantity of edible fats or oils or other edible oil-or fat-derived oleaginous material (5-32%) along with a quantity of emulsifier (0,5-5%) is added to an aqueous sugar solution (60-85% solids) to make up a syrup emulsion having a water content in the range of 9% -34% by weight. The edible fat or oil and emulsifier are added to the aqueous syrup at a temperature ranging from 115° F., to 155° F. (46.1 C. to 68.3 C.), and after emulsification, the mixture is heated to about 180° F. (82.2 C.). As in the above example, this invention does not provide for the characteristics of either liquid product homogeneity or self-emulsification and demonstrates a relatively high viscosity, which makes it inapplicable to this invention. In addition it provides for an oil-in-water emulsion whereas the composition claimed herein is a liquid homogeneous (solution or microemulsion) product.

SUMMARY OF THE INVENTION

The current invention involves the development of cold (0 C.), room temperature (about 20 -25 C.), and heat (e.g. about 50 C.) stable systems comprising mixtures of a concentrated liquid) saccharide product with an agricultural spray oil. These mixtures remain homogeneous liquids within the temperature range of about 0°-50° C. and are self-dispersing upon dilution in oil. The described homogeneous liquids contain amounts of 0.5-50% by weight surfactant with oil:saccharide product ratios between 1:100 and 100:1 with the preferred composition occurring between 1:10 and 10:1; the more preferred composition between 1:3 and 3:1; and the most preferred composition occurring between 1:2 and 2:1.

The invention comprises the basic components of: a biologically efficacious oil, a liquid saccharide product (which are primarily concentrated, viscous water based syrups), and one or more surfactants to deliver a stable, water dispersible, and homogeneous (solution or microemulsion) delivery system for agricultural adjuvants. One specific surfactant composition or surfactant chemical type is not universally required; using the understanding of interactions that was developed, a broad range of surfactant compositions were developed that were capable of delivering the described product.

Surfactant compositions that were used to develop such formulations include but are not limited to alkylpolysaccharides, phosphate esters, sorbitan esters, mono- and diglycerides, polysorbates, and ethoxylated alkylamines. Minor amounts of water may be used to effect the compatibilization of oil:surfactant:saccharide systems; in no case was more than 25% water added to effect compatibilization. Surfactant systems providing the desired homogeneity and compatibility were typically used in the range of 10-40% with the more preferred compositions containing 10-35%; and the most preferred compositions containing 10-25%.

Preferably the surfactant includes a non-ionic surfactant and is most preferably made entirely of one or more non-ionic surfactants. If desired, other surfactants, such as at least one anionic surfactant, for instance an anionic alkanolamine salt may be employed.

This invention relates to surfactant compositions and in particular to compositions which contains a plurality of surfactants and at least one oil, and which is readily emulsifiable into water.

The invention provides a concentrate composition which comprises:
a) at least one oil component;
b) at least one non-surfactant saccharide,
c) at least one non-ionic surfactant.

The composition may also comprise at least one of the following:
d) at least one surfactant hydrocarbyl saccharide; or
e) at least one anionic surfactant; or
f) at least one additional oil soluble non-ionic surfactant.

DETAILED DESCRIPTION OF THE INVENTION

The composition of the invention typically takes the form of an oil-based concentrate which is homogenous for at least 24 hours and which emulsifies readily on dilution into water. It will be used as a precursor for dilution with water for agricultural spray mixtures containing an agrochemical. Such spray mixtures will contain one or more pesticidally active ingredients and/or nutrients.

The concentrate composition may also comprise a water miscible liquid, which may be desirable if the viscosity of the composition would otherwise be inconveniently high. Such liquid may include or be water. The water content is preferably low enough for the composition to remain homogenous for at least 24 hours after being made. The components and their proportions are preferably chosen such that where any components are readily available only as aqueous solutions, such as HFCS (high fructose corn syrup), the composition provided by mixing the composition components is stable, notwithstanding the water which is thereby introduced. When the concentrate composition includes water, the concentrate will usually be a solution of the water in the oil, the surfactant combination acting to solubilise the water, or as a water-in-oil colloidal emulsion or a microemulsion in which the water is dispersed as very fine droplets such that the composition is clear or transparent.

The oil component typically has a boiling point of over about 200° C. at atmospheric pressure and a melting point not higher than about 60° C. It may comprise for example a mineral oil, an optionally hydrogenated vegetable oil, such as an optionally hydrogenated cotton seed oil, linseed oil, mustard oil, neem oil, niger seed oil, oiticica oil, olive oil, palm oil, palm kernel oil, peanut oil, perilla oil, poppy seed oil, rape seed oil, safflower oil, sesame oil, or soybean oil as well as an ester (especially a $C_1$ to $C_6$ ester) of a $C_8$ to $C_{22}$ fatty acid (especially a $C_{12}$ to $C_{18}$ fatty acid) e.g. methyl, ethyl or propyl laurate, myristate, palmitate, palmitoleate, linoleate, linolenolate, stearate or oleate, or a mixture thereof, e.g. an ester in which the total number of carbon atoms in the molecule does not exceed 20, and preferably an ester of a $C_{12}$ to $C_{18}$ fatty acid, e.g. methyl, ethyl or propyl laurate, or a mixture thereof.

The oil component preferably also contains or is associated with at least one oil soluble surfactant, especially one that can render the oil self-emulsifiable into water. Such a surfactant may include at least one of relatively high HLB (hydrophilic lipophilic balance) in combination with one of low HLB, for example calcium stearate. Such an oil solution component may be in the form of a commercially available so-called "crop oil" or "oil adjuvant". A typical oil component contains about 99 to about 45, preferably about 90 to about 60, parts by weight of oil, and about 1 to about 55, preferably about 10 to about 40, parts by weight of oil soluble surfactant(s). When water is present in solublised form or as a colloidal emulsion or a microemulsion the oil soluble surfactant may be partitioned between oil phase and aqueous phases (or be present at the interface).

The liquid saccharide solution may be of a monosaccharide, oligosaccharide or a polysaccharide or mixture thereof; saccharides may be linear, branched, or cyclic in nature. For such liquid saccharide solutions, the solvent may be water, propylene glycol, or glycerol or any combination thereof. It is conventional to refer to liquid saccharide solutions as syrups. Oligosaccharides present in solution are commonly identified as maltodextrins while polysaccharides are commonly identified as dextrins. Among liquid saccharide solutions, compounds of particular use in this invention include compounds and mixtures of compounds described as HFCS, corn syrup, corn sweetener, invert sugar, invert sugar syrup, sugar, sugar syrup, and maltodextrins where the resulting liquid saccharide solution is homogeneous and stable for at least 24 hours and contains about 75 parts by weight of water or less, preferably about 15 to about 50 parts by weight of water.

It is desirable that when the saccharide is an oligosaccharide of the general formula:

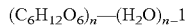

$(C_6H_{12}O_6)_n$—$(H_2O)_{n-1}$ where n is greater than or equal to one and not more than fifty. In particular, the saccharide may be one in which the average value of n is typically at least 1 and not more than 5. A particularly useful material of this type is one in which n has an average value of approximately 1 and where the saccharide is a monosaccharide and the monosaccharide is a keto-sugar, most preferably fructose. Fructose is commercially available as HFCS and the material designated for example as IsoClear 55 by Cargill can be used satisfactorily.

The non-ionic surfactant(s) may be any which will give a composition which is stable and homogeneous for at least 24 hours after being made.

Preferred non-ionic surfactants are of the formula:

$$R^1.O.A_nR^2 \qquad (I),$$

or

$$R^3N.(A_nR^2)_2 \qquad (II)$$

wherein
$R^1$ is a hydrocarbyl, hydrocarbonyl, or hydrocarbamidyl group, which suitably contains from 6 to 24, preferably 8 to 22, and especially 12 to 18 carbon atoms, a glycerol or polyglycerol group, or a sorbitan or sorbitol group;
A is a polyalkylene oxide unit containing an average of n alkylene oxide groups or mixed alkylene oxide groups, where the alkylene groups each have 2 to 8, preferably 2 or 3, carbon atoms;

n is between 0 and 40, preferably between 2 and 30, and most preferably between 5 and 20;

$R^2$ is hydrogen or hydrocarbonyl residue having 8 to 22 carbon atoms, or a polycarboxylic acid residue having 2 to 6 carbon atoms such as malate, fumarate, maleate, succinate, or citrate, or an oligomer thereof;

$R^3$ is a hydrocarbyl or hydrocarbonyl group having 8 to 22 carbon atoms, preferably 12 to 18.

The surfactant hydrocarbyl saccharide may be any which will give a composition which is stable and homogeneous for at least 24 hours after being made.

The surfactant hydrocarbyl saccharide may be a monoglycoside or a polyglycoside or mixture thereof It is conventional to refer to hydrocarbyl saccharide surfactants as hydrocarbyl polysaccharides even where the saccharide moiety only contains one saccharide unit. Typically such surfactants are mixtures of compounds with monosaccharide and polysaccharide (including disaccharide) units. Among glycosides, compounds of particular use in this invention include compounds and mixtures of compounds of the formula:

$$ROG_a$$

where

R is a hydrophobic moiety;

G is a saccharide residue; and a has an average value of at least 1.

The group R may be an optionally substituted hydrocarbyl group. In particular R can be an alkyl, cycloalkyl, aryl, alkaryl, aralkyl or alkenyl group and is preferably an alkyl group. The group R suitably contains from 4 to 30 carbon atoms, preferably up to 24 carbon atoms, more preferably from 6 to 18 carbon atoms and especially from 8 to 14 carbon atoms. Thus, R can be a mixture of alkyl or alkoxy groups which contain, on average, for example 8 to 14 carbon atoms.

The saccharide residue G may be derived from one or more of fructose, glucose, mannose, galactose, telose, gulose, allose, altrose, idose, arabinose, xylose, lyxose and ribose or from mixtures thereof. The group G is conveniently derived from glucose units and the glycoside is then a glucoside. If derived from sucrose the groups will comprise fructose and glucose residues.

The value of a is the degree of polymerisation. It typically has an average value of at least 1.1, preferably at least 1.2 and especially at least 1.3. The value of a is typically not greater than 8, and preferably not greater than 4, for example not greater than 2. When the glycoside is an alkyl glucoside, the value of a is conveniently between 1 and 2.

Desirable results are obtained when the glycoside is an alkyl polyglueoside of the general formula:

$$C_nH_{(2n+1)}.O.(C_6H_{10}O_5)_b.H$$

where n is from 8 to 14, and b is greater than one and not more than two.

In particular, the glucoside may be one in which the average value of n is from 9 to 13 and especially about 10. The value of b is typically at least 1.3 and not more than 1.9. A particularly useful material of this type is one in which n is from 8 to 11 and has an average value of 10 and b is about 1.35. Surfactant hydrocarbyl saccharides are commercially available and the materials designated for example as Atplus 452 and Atplus 438 by Uniqema or as sold under the trade name Triton BG 10 by Dow Chemicals can be used satisfactorily.

The anionic surfactant(s) may be any which will give a composition which is stable and homogeneous for at least 24 hours after making up.

The anionic surfactant(s) may be any which will give a composition which is stable and homogeneous for at least 24 hours after making up. It is characterized as at least one anionic surfactant compound of the general formula:

$$R^1.O.A_n\text{-}X \qquad (I),$$

or $$R_1\text{-}X \qquad (II)$$

where $R^1$ is a hydrocarbyl group having 6 to 24 carbon atoms, preferably 8 to 22 carbon atoms, and most preferably 12 to 18 carbon atoms;

A is a polyalkylene oxide unit containing an average of n alkylene oxide groups or mixed alkylene oxide groups, where the alkylene groups each have 2 to 8, preferably 2 or 3, carbon atoms;

n is between 0 and 60, preferably between 2 and 30, and most preferably between 3 and 15;

X is a group including at least one acidic H atom or salt thereof, desirably an amine salt.

In the foregoing formula X is a group including at least one acidic atom or a salt thereof, by which is meant that the group X can be ionized to form an anionic group in an aqueous medium. The group thus provides an anionic function, thereby making the surfactant anionic. This function can be a partially or fully oxidized phosphorus, sulfur, or carbon acid group.

The other non-ionic surfactant(s) may be any which will give a composition which is stable and homogeneous for at least 24 hours after being made.

Desirable results are particularly obtained when the non-ionic surfactant is of the general formula (I) or (II):

$$R^1.O.A_nR^2 \qquad (I),$$

or $$R^3N.(A_nR^2)_2 \qquad (II)$$

wherein $R^1$ is a hydrocarbyl, hydrocarbonyl, or hydrocarbamidyl group, which suitably contains from 6 to 24, preferably 8 to 22, and especially 12 to 18 carbon atoms, a glycerol or polyglycerol group, or a sorbitan or sorbitol group;

A is a polyalkylene oxide unit containing an average of n alkylene oxide groups or mixed alkylene oxide groups, where the alkylene groups each have 2 to 8, preferably 2 or 3, carbon atoms;

n is between 0 and 40, preferably between 2 and 30, and most preferably between 5 and 20;

$R^2$ is hydrogen or a hydrocarbonyl group having 8 to 22 carbon atoms, or a polycarboxylic acid residue having 2 to 6 carbon atoms such as malate, fumarate, maleate, succinate, or citrate, or an oligomer thereof;

$R^3$ is a hydrocarbyl or hydrocarbonyl group having 8 to 22 carbon atoms, preferably 12 to 18.

The relative proportions of the oil component (a), the liquid saccharide solution (b), and the non-ionic surfactant (c) are suitably (by weight):

a) 10 to 90, especially 25 to 75, preferably 30 to 60, b) 10 to 90, especially 15 to 45, preferably 20 to 40, and c) 5 to 80, especially 5 to 60, preferably 10 to 45; and optionally at least one surfactant hydrocarbyl saccharide (d); or anionic surfactant (e); or non-ionic surfactant (f), the proportions are as follows:

d) 1 to 20, especially 2 to 15, preferably 3 to 10, or e) 1 to 20, especially 2 to 15, preferably 3 to 10, or f) 1 to 20, especially 2 to 15, preferably 3 to 10.

Any chemical agent specific to the intended use of the composition will be an agrochemical. The agrochemical is typically one or more nutrients, growth regulators, herbicides, and/or pesticides, for example insecticides, fungicides or acaricides.

The invention includes a process for making the composition of the invention which comprises mixing the components together.

The invention further includes a diluted formulation which comprises a composition comprising components (a), (b) and (c) according to the invention with from about 10 to about 10,000 times the weight of the composition of water. The concentrate compositions of the invention emulsify readily on dilution in water to form the formulation. At relatively low levels of dilution, the product will be an oil-in-water emulsion having a relatively high concentration of oil. This intermediate emulsion subsequently can be further diluted by water or an aqueous solution or suspension of other components desired in the final formulation.

The diluted formulations can be made up in various ways. Thus, a formulation comprising components other than (a), (b), (c) and optionally one or more of components (d), (e), or (f) and water, can be made up by simply mixing the composition of components (a), (b), (c) and optionally one or more of components (d), (e), or (f) with water.

In a further aspect, the invention provides a method of applying a formulation of the invention to a substrate. Embodiments of this method include a method of treating vegetation by applying to plants and/or soil such a formulation according to the invention which formulation comprises a specific chemical agent which is an agrochemical.

In this embodiment the agrochemical may be one or more growth regulators, herbicides, and/or pesticides, for example insecticides, fungicides or acaricides. This embodiment of the invention of the method of applying the formulation accordingly includes: a method of killing or inhibiting vegetation by applying the formulation which comprises a specific chemical agent which is one or more growth regulators and/or herbicides, and a method of killing or inhibiting plant pests by applying the formulation which comprises a specific chemical agent which is one or more pesticides, for example insecticides, fungicides or acaricides.

In this embodiment, the effect of the agrochemical, whether one or more growth regulators, herbicides, and/or pesticides, for example insecticides, fungicides or acaricides, may be potentiated by the oil component and/or the saccharide and/or the surfactant composition present in the composition.

Examples of the agrochemical which is typically one or more growth regulators, herbicides, and/or pesticides, for example insecticides, fungicides or acaricides, particularly growth regulators, herbicides, etc. include phosphonomethyl-n-carboxymethyl (PMCM) compounds and related compounds of the formula:

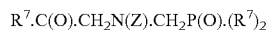

$$R^7.C(O).CH_2N(Z).CH_2P(O).(R^7)_2$$

where
each $R^7$ is independently halogen, —NHOH, —N$(R^8)_2$, —OR$^9$, —SR$^9$ or —OM, where
$R^8$ is independently a hydrogen, or alkyl or hydroxyalkyl, preferably containing less than about 5 carbon atoms, alkenyl, preferably containing less than about 5 carbon atoms, or phenyl; each $R^9$ is independently hydrogen, alkyl, hydroxyalkyl or chloroalkyl, preferably containing less than about 5 carbon atoms, alkoxy, preferably containing less than about 5 carbon atoms, alkylene amine, preferably containing less than about 12 carbon atoms, phenyl or benzyl; M is hydrogen or an agriculturally acceptable salt forming moieties such as alkali metal, alkaline earth metal, stannic, ammonium, organic ammonium, alkyl sulfonium, alkyl sulfoxonium, alkyl phosphonium moieties or combinations thereof; and Z is hydrogen, an organic moiety or an inorganic moiety.

Representative patents disclosing at least some of such compounds include U.S. Pat. Nos. 3799758, 4397676, 4140513, 4315765, 3868407, 4405531, 4481026, 4414158, 4120689, 4472189, 4341549 and 3948975. Patents disclosing PMCM compounds wherein Z is other than hydrogen include U.S. Pat. Nos. 3888915, 3933946, 4062699, 4119430, 4322239 and 4084954.

In preferred PMCM compounds,
Z is hydrogen or an organic substituent;
$R^9$ is independently selected from hydrogen, alkyl, hydroxyalkyl or chloroalkyl, preferably containing less than about 5 carbon atoms, alkoxy, preferably containing less than about 5 carbon atoms, alkylene amine, preferably containing less than about 12 carbon atoms, phenyl or benzyl moieties; and
M is selected from hydrogen and agriculturally acceptable salt forming moieties, alkali metal, phosphonium moieties or combinations thereof Representative patents disclosing at least some of such compounds include U.S. Pat. Nos. 3799758, 4397676, 4140513, 4315765, 3868407, 4405531, 4481026, 4414158, 4120689, 4472189, 4341549 and 3948975. Patents disclosing PMCM compounds wherein Z is other than hydrogen include U.S. Pat. Nos. 3888915, 3933946, 4062699, 4119430, 4322239 and 4084954.

In preferred PMCM compounds, Z is hydrogen or an organic substituent such as methylene carboxylic; methylene phosphonic; and methylene cyano. Other organic substituents include carboxyl, such as formyl, acetyl, benzoyl, perfluoroacyl and thiocarbonyl; ethylene, such as cyano, carbamoyl or carboxy substituted ethyl; and benzene sulphonyl substituents. Patents disclosing compounds where the nitrogen has three organic substituents include U.S. Pat. Nos. 3455675, 3556762, 3853530, 3970695, 3988142, 3991095, 3996040, 4047927, 4180394, 4203756, 4261727 and 4312662. A preferred tertiary nitrogen substituted PMCM compound is N,N-bis(phosphonomethyl)glycine.

Those PMCM compounds where Z is hydrogen are most preferred when the phytoactivity desired is herbicidal activity.

The above listed patents are incorporated herein by reference.

Illustrative examples of agriculturally acceptable salt forming moieties represented by M, as in OM, are the alkali metals having atomic weights of from 22 to 133, inclusive, such as sodium, potassium, or rubidium; the alkaline earth metals having atomic weights of from 24 through 88 inclusive, such as magnesium or calcium; ammonium and aliphatic ammonium, wherein the aliphatic is primary, secondary, tertiary or quatemary and preferably wherein the total number of carbon atoms does not exceed more than about twelve; phenylammonium; trialkylsulphonium, preferably wherein the total number of carbons in the three alkyl substituents does not exceed more than about six, such as trimethylsulphonium, ethyl dimethylsulphonium, propyl dimethylsulphonium and the like; trialkylsulphoxonium, preferably wherein the total number of carbon atoms in the three alkyl substituent does not exceed more than about six, such as trimethylsulphoxonium, ethyl dimethylsulphoxonium, propyl dinethylsulfoxonium and the like; tetraalkylphosphonium, such as tetramethylphosphonium, ethyl trimethylphosphonium, propyltrimethylphosphonium and similar groups.

In desirable compositions according to this invention, M is independently selected from the above described agriculturally acceptable salt forming moieties and hydrogen. In more desirable compositions, M is an alkali metal, ammonium, monoalkyl ammonium or trialkylsulphonium moiety. In especially desirable compositions only one M is an alkali metal, ammonium, monoalkyl ammonium, or trialkylsulphonium moiety, while the two M's are hydrogen.

Particularly desirable compositions include isopropylamine N-phosphonomethylglycine, trimethylsulphonium N-phosphonomethylglycine and sodium sesqui-N-phosphonomethylglycine. Combinations of two or more PMCM compounds can be employed in the composition formulation and methods of the present invention.

The following examples are illustrative of the present invention. All amounts are by weight unless otherwise indicated.

EXAMPLE 1

The following concentrate is prepared:

| Component code | Component Name | Wt. Amount |
|---|---|---|
| a | Mineral oil | 44.12 |
| b | High Fructose Corn Syrup solution | 29.41 |
| c | Ethoxylated tallowamine | 26.47 |

The foregoing concentrate self-emulsifies upon 5% dilution in water. When 0.5% (v/v) parts of the agrochemical glyphosate is incorporated into the concentrate prior to dilution in water the diluted composition is effective as a herbicide.

EXAMPLE 2

The following concentrate is prepared:

| Component code | Component Name | Wt. Amount |
|---|---|---|
| a | Mineral oil | 46.15 |
| b | High Fructose Corn Syrup | 15.38 |
| c | Ethoxylated tallowamine | 30.77 |
| d | $C_9$-$C_{11}$ alkylpolysaccharide | 7.69 |

The foregoing concentrate self-emulsifies upon 5% dilution in water. When 0.5% (v/v) parts of the agrochemical glyphosate is incorporated into the concentrate prior to dilution in water the diluted composition is effective as a herbicide.

EXAMPLE 3

The following concentrate is prepared:

| Component code | Component Name | Wt. Amount |
|---|---|---|
| a | Mineral oil | 45.45 |
| b | High Fructose Corn Syrup solution | 18.16 |
| c | Ethoxylated tallowamine | 30.30 |
| e | Dodecylbenzenesulfonate, isopropylamine salt | 6.06 |

The foregoing concentrate self-emulsifies upon 5% dilution in water. When 0.5% (v/v) parts of the agrochemical glyphosate is incorporated into the concentrate prior to dilution in water the diluted composition is effective as a herbicide.

EXAMPLE 4

The following concentrate is prepared:

| Component code | Component Name | Wt. Amount |
|---|---|---|
| a | Mineral oil | 42.55 |
| b | High Fructose Corn Syrup solution | 25.55 |
| c | Ethoxylated tallowamine | 28.37 |
| f | Sorbitan monooleate | 3.55 |

The foregoing concentrate self-emulsifies upon 5% dilution in water. When 0.5% (v/v) parts of the agrochemical glyphosate is incorporated into the concentrate prior to dilution in water the diluted composition is effective as a herbicide.

EXAMPLE 5

The following concentrate is prepared:

| Component code | Component Name | Wt. Amount |
|---|---|---|
| a | Mineral oil | 44.12 |
| b | High Fructose Corn Syrup solution | 14.71 |
| c | Ethoxylated tallowamine | 29.41 |
| d | $C_9$-$C_{11}$ alkylpolysaccharide | 8.82 |
| f | Mono- and di-glycerides | 2.94 |

The foregoing concentrate self-emulsifies upon 5% dilution in water. When 0.5% (v/v) parts of the agrochemical glyphosate is incorporated into the concentrate prior to dilution in water the diluted composition is effective as a herbicide.

EXAMPLE 6

The following concentrate is prepared:

| Component code | Component Name | Wt. Amount |
|---|---|---|
| a | Mineral oil | 43.17 |
| b | High Fructose Corn Syrup solution | 18.71 |
| c | Ethoxylated tallowamine | 28.78 |
| e | Dodecylbenzenesulfonate, isopropylamine salt | 7.19 |
| f | Sorbitan monooleate | 2.16 |

The foregoing concentrate self-emulsifies upon 5% dilution in water. When 0.5% (v/v) parts of the agrochemical glyphosate is incorporated into the concentrate prior to dilution in water the diluted composition is effective as a herbicide.

EXAMPLE 7

The following concentrate is prepared:

| Component code | Component Name | Wt. Amount |
|---|---|---|
| a | Mineral oil | 33.78 |
| b | High Fructose Corn Syrup solution | 14.93 |
| c | Ethoxylated tallowamine | 29.85 |
| d | $C_9$-$C_{11}$ alkylpolysaccharide | 7.46 |
| e | Dodecylbenzenesulfonate, isopropylamine salt | 2.99 |

The foregoing concentrate self-emulsifies upon 5% dilution in water. When 0.5% (v/v) parts of the agrochemical glyphosate is incorporated into the concentrate prior to dilution in water the diluted composition is effective as a herbicide.

EXAMPLE 8

The following concentrate is prepared:

| Component code | Component Name | Wt. Amount |
|---|---|---|
| a | Mineral oil | 37.97 |
| b | High Fructose Corn Syrup solution | 25.32 |
| c | Ethoxylated tallowamine | 25.32 |
| d | $C_9$-$C_{11}$ alkylpolysaccharide | 6.33 |
| e | Dodecylbenzenesulfonate, isopropylamine salt | 2.53 |
| f | Sorbitan monooleate | 2.53 |

The foregoing concentrate self-emulsifies upon 5% dilution in water. When 0.5% (v/v) parts of the agrochemical glyphosate is incorporated into the concentrate prior to dilution in water the diluted composition is effective as a herbicide.

One skilled in the art will appreciate that the present invention can be practiced by other than the described embodiments that are presented for purposes of illustration and not of limitation

The invention claimed is:

1. A method of making an agrochemical spray formulation, comprising:
   diluting a homogeneous and self-emulsifying oil-based agrochemical concentrate composition with water to form an agrochemical spray formulation that comprises an agrochemical;
   wherein the self-emulsifying oil-based agrochemical concentrate composition, comprises:
   a) from 30 to 60 parts by weight of at least one oil component;
   b) from 15 to 40 parts by weight of at least one non-surfactant saccharide, present in solution; and
   c) from 5 to 45 parts by weight of at least one non-ionic surfactant of the formula:

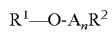 $R^1$—O-$A_nR^2$ (I), or

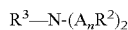 $R^3$—N-$(A_nR^2)_2$ (II); and d) at least one of the following additional components:
      i) from 1 to 20 parts by weight of at least one surfactant hydrocarbyl saccharide;
      ii) from 1 to 20 parts by weight of at least one anionic surfactant; or
      iii) from 1 to 20 parts by weight of at least one further non-ionic surfactant;
   wherein:
   $R^1$ represents a hydrocarbyl, hydrocarbonyl, or hydrocarbamidyl group having from 6 to 24 carbon atoms, a glycerol or polyglycerol group, or a sorbitan or sorbitol group;
   A represents a polyalkylene oxide unit containing an average of n alkylene oxide groups or mixed alkylene oxide groups, wherein the alkylene groups each have 2 to 8 carbon atoms;
   n represents between 0 and 40;
   $R^2$ represents hydrogen or hydrocarbonyl residue having 8 to 22 carbon atoms, or a polycarboxylic acid residue of malate, fumarate, maleate, succinate, or citrate, or an oligomer thereof; and
   $R^3$ represents a hydrocarbyl or hydrocarbonyl group having 8 to 22 carbon atoms; and
   wherein the total surfactant comprises from 10% to 50% by weight of the concentrate.

2. The method of claim 1, wherein the homogeneous and self-emulsifying oil-based agrochemical concentrate composition, comprises each of the at least one of the additional components of d).

3. The method of claim 1, wherein the at least one of the additional components d) is present in an amount of from 2 to 15 parts by weight.

4. The method of claim 1, wherein the at least one of the additional components d) is present in an amount of from 3 to 15 parts by weight.

5. The method of claim 1, wherein the homogeneous and self-emulsifying oil-based agrochemical concentrate composition, comprises:
   a) from 30 to 60 parts by weight of at least one oil component;
   b) from 15 to 40 parts by weight of at least one non-surfactant saccharide; and
   c) from 5 to 45 parts by weight of a surfactant component including a hydrocarbyl amine ethoxylate.

6. The method of claim 1, wherein the oil component of the homogeneous and self-emulsifying oil-based agrochemical concentrate composition has a boiling point of over 200° C.

7. The method of claim 1, wherein the oil component of the homogeneous and self-emulsifying oil-based agrochemical concentrate composition, comprises:
   a mineral oil, a vegetable oil, an ester of a $C_8$ to $C_{22}$ fatty acid, or a mixture thereof.

8. The method of claim 1, wherein the non-surfactant saccharide component of the homogeneous and self-emulsifying oil-based agrochemical concentrate composition is selected from the group consisting of: a monosaccharide, an oligosaccharide and a polysaccharide.

9. The method of claim 1, wherein the agrochemical spray formulation comprises
   15 to 45 parts by weight of total surfactant.

10. The method of claim 1, wherein the non-ionic surfactant component of the homogeneous and self-emulsifying oil-based agrochemical concentrate composition is selected from the group consisting of: an alkoxylated fatty acid, a polyalkylene glycol ester, an alkoxylated glyceride, an alkoxylated sorbitan ester, a alkoxylated sorbitol ester, an alkylphenol alkoxylate, an alcohol alkoxylate, an alkylamine alkoxylate, an alkanolamide, and an alkoxylated alkanolamide.

11. The method of claim 1, wherein:
i) the at least one surfactant hydrocarbyl saccharide component is of the formula:

$$ROG_a$$

wherein:
R represents a hydrophobic moiety;
G represents a saccharide residue; and
a represents an average value of at least 1;
ii) the at least one anionic surfactant component is of the formula:

$$R^1-O-A_n-X \quad \text{(I), or}$$

$$R^1-X \quad \text{(II)}$$

wherein:
R¹ represents a hydrocarbyl group having 6 to 24 carbon atoms;
A represents a polyalkylene oxide unit containing an average of n alkylene oxide groups or mixed alkylene oxide groups, where the alkylene groups each have 2 to 8 carbon atoms;
n represents between 0 and 60; and
X represents a group including at least one acidic H atom or salt thereof; and
iii) the at least one further non-ionic surfactant component is of the formula:

$$R^1-O-A_nR^2 \quad \text{(I), or}$$

$$R^3-N-(A_nR^2)_2 \quad \text{(II); and}$$

wherein:
R¹ represents a hydrocarbyl, hydrocarbonyl, or hydrocarbamidyl group having from 6 to 24 carbon atoms, a glycerol or polyglycerol group, or a sorbitan or sorbitol group;
A represents a polyalkylene oxide unit containing an average of n alkylene oxide groups or mixed alkylene oxide groups, where the alkylene groups each have 2 to 8 carbon atoms;
n represents between 0 and 40;
R² represents hydrogen or a hydrocarbonyl group having 8 to 22 carbon atoms, or a polycarboxylic acid residue of malate, fumarate, maleate, succinate, or citrate, or an oligomer thereof; and
R³ represents a hydrocarbyl or hydrocarbonyl group having 8 to 22 carbon atoms.

12. The method of claim 11, wherein:
the at least one alkyl polysaccharide component is an alkyl polyglucoside of the general formula:

$$C_nH_{(2n+1)}-O-(C_6H_{10}O_5)_bH$$

where n is from 8 to 14 and b is greater than or equal to one and less than three.

13. The method of claim 11, wherein the at least one anionic surfactant component is selected from the group consisting of: an alkyl carboxylate, an alkyl sulphate, an alkyl ether sulfate, an alkyl phosphate, an alkyl ether phosphate, an alkyl sulfosuccinate, an alkyl ether sulfosuccinate, an alkyl sulfonate, and an alkyl phosphonate.

14. The method of claim 11, wherein at least one further non-ionic surfactant component is selected from the group consisting of: a glycerol ester, a polyglycerol ester, a sorbitol ester, a sorbitan ester, an ethylene glycol ester, a propylene glycol ester, a polyethylene glycol ester, and a fatty alcohol.

15. The method of claim 1, wherein the agrochemical is a herbicide.

16. The method of claim 1, wherein the agrochemical comprises one or more growth regulators, herbicides, and/or pesticides.

17. The method of claim 1, wherein the water used to dilute the concentrate is present in the agrochemical spray formulation in an amount from 10 to 10,000 times the weight of the concentrate composition.

18. A method of treating vegetation, comprising applying to the vegetation and/or soil the agrochemical spray formulation prepared by the method of claim 1.

19. The method of claim 15, wherein the agrochemical comprises at least one phosphonomethyl-N-carboxymethyl herbicide of the formula:

$$R^1.C(O).CH_2N(Z).CH_2P(O).(R^1)_2$$

wherein:
R¹ independently represents halogen, —NHOH, —N(R²)₂, —OR³, —SR³ or —OM,
R² independently represents hydrogen, alkyl, hydroxyalkyl, alkenyl, or phenyl;
R³ independently represents hydrogen, alkyl, hydroxyalkyl or chloroalkyl, alkoxy, alkylene amine, phenyl or benzyl;
M represents a hydrogen or an agriculturally acceptable salt forming moiety, such as alkali metal, alkaline earth metal, stannic, ammonium, organic ammonium, alkyl sulfonium, alkyl sulfoxonium, alkyl phosphonium moiety, or combination thereof; and
Z is hydrogen, an organic moiety, or an inorganic moiety.

20. A method of making an agrochemical spray formulation, comprising:
diluting a homogeneous and self-emulsifying oil-based agrochemical concentrate composition with water to form an agrochemical spray formulation that comprises an agrochemical;
wherein the self-emulsifying oil-based agrochemical concentrate composition comprises:
(a) at least one oil component;
(b) at least one non-surfactant saccharide; and
(c) 0.5% to 50% by weight of at least one non-ionic surfactant; and
wherein:
(i) the weight ratio of said oil to said non-surfactant saccharide is between 1:100 to 100:1; and
(ii) said concentrate composition is homogeneous for at least 24 hours.

* * * * *